(12) United States Patent
Taverni et al.

(10) Patent No.: US 12,048,555 B1
(45) Date of Patent: Jul. 30, 2024

(54) MEASURING SYSTEM FOR MEASURING A SURFACE OF AN OBJECT OR SKIN OF A PERSON

(71) Applicant: HEXAGON TECHNOLOGY CENTER GMBH, Heerbrugg (CH)

(72) Inventors: Gemma Taverni, Zürich (CH); Hakki Karaman, Uster (CH); Stefan Geissbühler, Langenthal (CH); Simon Mark, Thal (CH); Zheng Yang, Friedrichshafen (DE); Burkhard Böckem, Jonen AG (CH); Lukas Buchmann, Zürich (CH); Sandra Tobler, Berneck (CH); Jan Glückert, Lindau (DE); Markus Wettstein, Wädenswil (CH)

(73) Assignee: HEXAGON TECHNOLOGY CENTER GMBH, Heerbrugg (CH)

( * ) Notice: Subject to any disclaimer, the term of this patent is extended or adjusted under 35 U.S.C. 154(b) by 0 days.

(21) Appl. No.: 18/230,374

(22) Filed: Aug. 4, 2023

Related U.S. Application Data

(63) Continuation of application No. PCT/EP2023/066078, filed on Jun. 15, 2023.

(51) Int. Cl.
*A61B 5/00* (2006.01)

(52) U.S. Cl.
CPC ............ *A61B 5/441* (2013.01); *A61B 5/0075* (2013.01); *A61B 5/0079* (2013.01); *A61B 5/742* (2013.01)

(58) Field of Classification Search
CPC ..... A61B 5/441; A61B 5/0075; A61B 5/0079; A61B 5/742; A61B 5/44; A61B 5/0059; A61B 5/0077; A61B 5/74; F21V 7/00; F21V 7/0008; F21V 7/0025; F21V 7/0033; F21V 7/0041; F21V 99/00
See application file for complete search history.

(56) References Cited

U.S. PATENT DOCUMENTS

| | | | |
|---|---|---|---|
| 10,652,520 B2 | 5/2020 | Otto et al. | |
| 2005/0200963 A1* | 9/2005 | Hoke | G02B 27/026 |
| | | | 359/630 |

(Continued)

FOREIGN PATENT DOCUMENTS

| | | |
|---|---|---|
| AU | 2011253652 A1 | 12/2011 |
| WO | 2022/263214 A1 | 12/2022 |

OTHER PUBLICATIONS

International Search Report and Written Opinion of the International Searching Authority dated Feb. 26, 2024 as received in Application No. PCT/EP2023/066078.

*Primary Examiner* — Bao Q Truong
(74) *Attorney, Agent, or Firm* — Maschoff Brennan

(57) ABSTRACT

A capture device for imaging a person, in particular the face or a part of the face of the person, the capture device comprises at least one camera for capturing an image of the person. The capture device comprises an infinity mirror comprising at least two mirror surfaces arranged oppositely from each other, a light source for emitting light, and a front side to look inside the infinity mirror. The infinity mirror is arranged at the capture device and placed and oriented relative to the capture device so that a capture range with an insight axis and an insight distance for the person is defined and defined capturing of the person by means of the at least one camera is provided when the person is positioned according to the capture range.

18 Claims, 4 Drawing Sheets

(56) References Cited

U.S. PATENT DOCUMENTS

| | | | |
|---|---|---|---|
| 2008/0252758 A1* | 10/2008 | Manley | F41G 3/2605 |
| | | | 348/262 |
| 2010/0141781 A1* | 6/2010 | Lu | G06V 40/67 |
| | | | 348/222.1 |
| 2011/0206254 A1 | 8/2011 | Patwardhan | |
| 2011/0304705 A1 | 12/2011 | Kantor et al. | |
| 2019/0035080 A1 | 1/2019 | Bisker | |
| 2023/0022108 A1 | 1/2023 | Ghosh et al. | |

* cited by examiner

MEASURING SYSTEM FOR MEASURING A SURFACE OF AN OBJECT OR SKIN OF A PERSON

FIELD OF THE DISCLOSURE

The present disclosure relates generally to systems and methods for determining surface information of an object, in particular of the skin of a person, based on optical measurements.

BACKGROUND

In the field of (cosmetic) treatment of a person, in particular the skin of the person, assessment of skin conditions has become an important factor to apply a suitable treatment to a proper extent. In particular concerning skin treatment or concerning a procedure to change the appearance of the skin, visual assessment based on captured images of the person is a preferred approach.

Such visual information can typically be acquired for aesthetic procedures, surgical procedures or, as mentioned, for assessment of skin conditions. For example, a number of new face rejuvenating procedures join the existing approaches in the aesthetic industry every year; these may include without limitation pharmacology based topical solutions, minimally invasive and invasive surgery, and energy-based treatments such as laser and other photon based systems, ultrasound approaches, radio frequency, cold (cryo), microwave, and Multiple Energy Delivery Systems (IVIES).

An optical acquisition of image or three-dimensional (3D) information of a human body typically entails the use of a particular camera setup and light sources, arranged relative to the person. Preferably, the cameras and light sources are activated while the person remains still. The number of cameras and light sources required typically depends in direct relation on the size of the area to be imaged and/or on the accuracy to be reached.

Several concepts are known for capturing surface information related to a human body, e.g. body data related to a face or other part of a body of a person. For example, U.S. Pat. No. 10,652,520 B2 proposes a body scanner having a number of capturing groups for acquiring body surface information by illuminating the body and capturing the body while illuminated.

In many aesthetic procedures, such as topical or energy-based face rejuvenation, the subject does not exhibit immediate positive results from the treatment and must wait an extended period of time, potentially receiving additional treatments to complete the procedure.

It would be advantageous to provide an estimate to the subject of the expected results after a certain amount of time has passed. Before and after graphics of previously treated subjects are known, but the current subject would best be served seeing the projected results on his/her own image.

It should be noted that when observing human subjects, change detection is particularly challenging. Changes in a subject's perceived appearance result from a complex combination of factors such as age-specific variations, pathological changes, physical movement, physical appearance variations, etc., in addition to changes in lighting conditions and differences between the devices with which the images are captured. This is further complicated when images are captured under different imaging modalities (e.g., cross-polarised, parallel-polarised, fluorescence, etc.), which result in images that look very different from images captured under standard white-light illumination. Comparing images across time, modality, and/or capture devices is thus a very challenging problem.

Therefore, there is a need to provide a method and system which enables to track changes of the person's skin very accurately and with basically repeatable measuring conditions.

Furthermore, for applying a recommended aesthetic procedure detailed knowledge about the person's skin at least in a region of interest may be required. The region of interest typically can be a comparatively small part of the person's body like small wrinkles in the person's face.

With view to surgical procedures similar requirements apply. Information about body or skin conditions at a particular region of interest, e.g. a region of the person's body at which a surgical intervention should be performed, is highly desired. Such body information about that specific region should typically be of an increased information level compared to neighbouring body parts.

Appearance or observation of particular skin properties typically depends on a sensor setup, e.g. the type of measuring light which is used for measuring the skin, and/or on illumination conditions, e.g. an incidence angle of used illumination light. Existing systems are for instance capable of capturing images which provide to derive surface information to a limited extent. This may be the case if the type of measuring light is not suitable to measure a particular skin property or if an illumination is set to be advantageous for a particular skin property which is not of current interest.

Moreover, a further downside of known solutions for measuring a person is that the existing devices often comprise comparatively complex design and limited flexibility. Moreover, the devices are designed for measuring a person one-time which results in comparatively great effort for precise comparing e.g. a development of a treatment over time.

OBJECT OF THE DISCLOSURE

Therefore, it is an object of the disclosure to provide an improved measuring device, system and method which provides improved acquisition of surface data of a person.

A further object of the present disclosure is to provide a measuring approach capable of providing improved and repeatable measuring data with respect to measuring at last a part of a human body.

SUMMARY

The disclosure relates to a capture device and system for measuring an object like the skin of a human body. The system is designed and configured to derive visual and topological (topographic) information of the skin related to skin properties of a person's skin by means of optical measurement. The derived skin properties may be directed to beauty aspects like winkles and pores of the skin, in particular concerning amounts, densities, sizes and appearances, and/or may be directed to other aspects like skin condition.

The measuring system comprises at least the capture device (measuring device) and a controlling and processing unit, in particular a display device.

The controlling and processing unit can be embodied as a single component arranged together with (e.g. in) the capturing device or display device or being physically separated therefrom. The controlling and processing unit may alternatively or additionally be implemented to provide several components, the components preferably being configured for exchanging information with each other. The controlling and processing unit can be configured for bi-directionally transmitting (sending and receiving) signals (information) to and from the capturing device and/or the display device. The controlling and processing unit can be provided by an algorithmic processing device like a computer, a tablet, a smart phone, a (web or network) server or the like. In particular, the controlling and processing unit can be provided by a data-storing and/or data-processing cloud.

The capture device comprises light emitting units and image capturing units which both provide light emitting and image capturing by means of circularly polarising emitted or received light. A significant advantage of using circularly polarised light for measuring the object instead of linearly polarised light as known for prior art is that for acquiring surface data of regions of the object which are not reflective circularly polarised light provides surface information also from such regions which do not fully meet linear polarising requirements. In other words, if using linearly polarised light only part of the object may be measured while image information for almost the entire object is accessible when using circularly polarised light.

Another advantage of the disclosure is that using circular patterns allows normals to be estimated simultaneously from any number of viewpoints. In linear polarisation there is always a preferred illumination direction. For a single viewpoint, it is possible to circumvent this problem by placing the discontinuities at the Brewster angle; however, this cannot be accomplished for multiple cameras at the same time. Hence, according to the disclosure, circular polarisation is used for obtaining view-independent diffuse/specular separation.

Accordingly, the disclosure relates to a measuring system for measuring an object, in particular the skin of a person. The measuring system comprises a capture device comprising a set of illumination elements for illuminating the object and a set of cameras for capturing an image of the object. The system further comprises a controlling and processing unit. The capture device can be provided by one single device which comprises the set of illumination elements and the set of cameras or can be provided by multiple (at least two) sub-devices which each comprises a part of the illumination elements and/or the cameras.

The controlling and processing unit comprises at least a data acquisition functionality which is configured to provide surface data by activating at least a part of the illumination elements for illuminating the object with measuring light and capturing at least one image by detecting measuring light reflected at the object by means of at least a part of the set of cameras. In this context, the term reflected should comprise any interaction of the measuring light with the object which results in at least a part of the measuring light comprising a different propagation direction after interacting with the object, i.e. should also include scattering and deflection. The controlling and processing unit also comprises a 3D-modelling functionality which is configured to provide a 3D model of the object by processing the surface data.

A first group of the set of illumination elements comprises circular polarised filtering of a first circulation direction for emitting the measuring light as circularly polarised measuring light of the first circulation direction and a first group of the set of cameras comprises circular polarised filtering of the first circulation direction for receiving reflected circularly polarised measuring light of the first circulation direction, the first group of the cameras comprises at least a first and a second camera.

It should be understood that the first group of illumination elements and/or the first group of cameras can provide the whole set of illumination elements or cameras, respectively. Alternatively, the first group of illumination elements and/or the first group of cameras each comprise a part of the respective set of components.

The data acquisition functionality is configured to provide the surface data by activating the first group of the illumination elements for illuminating the object with the (circularly polarised) measuring light and capturing the at least one image by detecting (circularly polarised) measuring light reflected at the object by means of the first group of the cameras.

The surface data can comprise image data, point cloud data and/or texture data. The texture data can be provided by at least one of specular data, albedo data, normal data and displacement data, in particular by at least one of a specular map, an albedo map, a normal map and a displacement map.

By providing the same circular polarising direction on side of the illumination elements and the cameras the setup is preferably configured to detect diffusely scattered measuring light. For detection of the diffusely scattered and circularly polarised measuring light, a polarising filter having a quarter wave plate and a liner polarising filter can be provided at each of the cameras. The same filtering arrangement can be comprised by the illumination elements to first generate linearly polarised light by a linear polarising filter and then changing the polarisation from linear to circular by means of a quarter wave plate. The linear polarising direction of the linear polarising filter of the illumination elements here is arranged perpendicular to the polarising direction of the linear polarising filter of the cameras. This is because the linear polarising direction would change by 90° after changing the polarisation back from circular to linear.

The above applies in case of diffuse scattering since the circular polarisation direction does not change, e.g. from right-handed to left-handed or vice versa.

In particular, detection of diffuse scattering can provide to generate an albedo map of the object.

In one embodiment the set of cameras of the capture device can comprise additional texture cameras which are arranged and configured to acquire texture image data which can be used to supplement, to support or to generate texture data, e.g. a normal map or albedo map, related to the object. The texture data can additionally be processed to generate the 3D model.

In one embodiment, the first group of the set of illumination elements can be provided to emit or project a pattern, e.g. a random-dot pattern is amongst others one option. The first and/or the second camera can accordingly acquire the pattern projected on the object. Such arrangement can be understood to be implemented as a single-shot triangulation sensor with active-mono (structured light) or active-stereo system. "Active" is referred to as active projection of specific patterns, whereas "mono" and "stereo" stand for number of cameras used. The density and size of local feature is correlated to the achieved lateral resolution and can be optimised with dedicated coding and matching technologies, such as binary coding, colour coding, speckle pattern etc.

Each local feature of the observed pattern can unambiguously be identified and assigned with individual pre-calibrated pixel-to-depth curve.

In contrast, the identification of local feature can be necessary for passive-stereo systems (no projection of a pattern). The pixel coordinates in both cameras looking at the same local feature must be localised by matching algorithm. In one embodiment, the cameras and illumination elements are configured to provide a passive-stereo system, e.g. based on stereo-photogrammetry.

In one embodiment, the first group of illumination elements can be embodied to emit diffuse light.

However, the circular polarisation direction changes when the measuring light is reflected at the surface, which means that the linear polarising direction after changing back from circular to linear is parallel to the linear polarising direction of the linear polarising filter of the illumination elements. Hence, the above configuration is not capable to detect reflected measuring light and suppresses detection of reflective regions of the surface.

The relative circulation directions are preferably defined by particular arrangements of polarising filters on both sides, i.e. the illumination side and the capturing side. Filtering of identical circulation directions is provided in case the emitted circularly polarised illumination/measuring light can directly be received by the camera, i.e. the circulation direction of the measuring light has not changed. Filtering of opposite circulation directions is provided in case the emitted circularly polarised illumination/measuring light cannot directly be received by the camera, i.e. the circulation direction of the measuring light has first to be changed for proper detection.

In one embodiment the data acquisition functionality can be configured to provide the surface data comprising diffuse surface data, wherein the diffuse surface data is acquired by illuminating the object by activating the first group of the illumination elements and capturing at least one diffuse image by means of the first group of the cameras. In particular an image comprising a cross-polarised portion of the measuring light is captured as the diffuse image. Further, a point cloud is derived based on the at least one diffuse image. The 3D-modelling functionality can be configured to derive the 3D model based on the diffuse surface data.

In one embodiment, at least two diffuse images are captured by means of the first group of the cameras and the point cloud is derived based on the at least two diffuse images to provide the diffuse surface data, wherein a first of the at least two diffuse images is captured by the first camera and a second of the at least two diffuse images is captured by the second camera.

By acquiring the diffuse surface data with two (or more) cameras the measuring range can be extended accordingly and, as for example, a face of a person can be captured from different poses and sides. This allows to generate surface data of all regions of interest of the object (face).

In one embodiment the capture device can comprise a second group of the illumination elements which comprises circular polarised filtering of a second circulation direction, opposite to the first circulation direction.

In one embodiment a second group of cameras of the set of cameras can comprise circular polarised filtering of the second circulation direction, opposite to the first circulation direction, the second group of the cameras comprises at least a third and a fourth camera.

In one embodiment, the data acquisition functionality can be configured to provide the surface data comprising reflection surface data. The reflection surface data can be acquired by illuminating the object by activating the first group of illumination elements and capturing at least two reflection images by means of the second group of the cameras, or illuminating the object by activating the second group of illumination elements and capturing at least two reflection images by means of the first group of the cameras.

A first of the at least two reflection images is captured by the first or the third camera, respectively, and a second of the at least two reflection images is captured by the second or the fourth camera, respectively.

A point cloud can be derived based on the at least two reflection images, and the 3D-modelling functionality can be configured to derive or supplement the 3D model based on the reflection surface data. Additionally or alternatively, the at least two reflection images are referenced relative to each other in order to provide a reflection map of the object. In particular each reflection image comprises a parallel-polarised portion of the measuring light.

For detection of reflections at the object a configuration of opposite circular polarising directions is preferably used. The 3D model can be extended by additionally processing the point cloud which is derived based on the reflection images.

In one embodiment the data acquisition functionality can be configured to provide a specular map for the object. The specular map is derived by illuminating the object by activating the first group of illumination elements and capturing at least one diffuse image by means of the first group of the cameras, illuminating the object by activating either the first group of the illumination elements or the second group of the illumination elements and capturing at least one reflection image by means of either the second group of the cameras or the first group of the cameras, wherein illuminating the object is provided with circular polarised filtering of a circulation direction different from a circulation direction of circular polarised filtering for capturing the at least one reflection image and comparing the image data of the at least one diffuse image and the image data of the at least one reflection image. In particular wherein comparing the image data comprises subtraction of the image data of the at least one diffuse image and the image data of the at least one reflection image and/or providing a ratio between the image data of the at least one diffuse image and the image data of the at least one reflection image.

The specular map is derived based on the comparison of the image data, wherein the at least one diffuse image and the at least one reflection image at least partly cover a common part of the object.

A specular map may be black and white images that determine the shininess or reflectivity of an object in 3D. Such specular can be used in conjunction with a diffuse and normal map to enhance the realism of the object's texture.

Specular maps are used to define the shininess/highlight on the surface of the object. Typically, a specular map can be a black and white image that maps out the shininess value on an object. The whiter the pixel, the more shiny the object in that specific place on the texture. Therefore, textures that are not shiny and that are more matt like stone or fabrics would have a very dark specular map. While other more shiny materials like chrome or plastic would have very bright specular maps. Hence, a specular map can determine how much light will reflect off of the surface.

In one embodiment, the cameras of the set of cameras can be fixedly arranged relative to each other. The optical axis of the first camera is transversally oriented relative to the optical axis of the second camera and/or the optical axis of the third camera is transversally oriented relative to the optical axis of the fourth camera.

In particular, the optical axes of the first camera and the second camera, and/or the optical axes of the third camera and the fourth camera, respectively, enclose an angle between 80° and 100°, in particular an angle of 90°. In particular, the angle is enclosed by the optical axes when the optical axes are projected on a plane which is defined by at least one of the optical axes and a connecting line between the first camera and the second camera or between the third camera and the fourth camera, respectively.

The particular alignment of the optical axes of the cameras provide capturing of the object with at least two different poses, wherein the orientation is chosen so that a face can be captured from two sides and thus providing covering the whole face and also the neck of a person. Hence, surface data of the entire region of interest can be captured by one shot.

A point cloud which represents the whole region of interest (e.g. face and neck) can thus be generated by providing first surface data by the image data acquired with the first camera and second surface data by the image data acquired with the second camera. Both surface data can be provided in form of a point cloud. The surface data can be merged or fused by known image processing techniques or based on a point cloud level.

In one embodiment at least the first camera and/or the second camera, and/or the cameras of the second group of the cameras, can be provided as high-resolution monochromatic cameras. The camera(s) can comprise a filter element which is configured to transmit (only) light with a wavelength of the blue spectrum, in particular to transmit light with a wavelength out of a wavelength range between 380 nm and 500 nm, in particular between 420 nm and 480 nm, and to block transmission of light with a wavelength besides the blue spectrum, in particular to block light with a wavelength less than 380 nm and/or greater than 500 nm, in particular to block light with a wavelength out of a wavelength range between 500 nm and 1000 nm.

The advantage of using a combination of monochromatic cameras and a blue filter is that the surface data for generating a 3D model can be generated with super high resolution and accuracy and a more dens point cloud can be provided. This results in a 3D model which comprises correspondingly a mesh of higher density (e.g. smaller meshes) and greater accuracy. Processing of the monochromatic data can further be performed with few effort.

In particular, two optimally placed high-resolution monochromatic cameras with blue filter can cover >80% of the target surface for high-resolution texture for panchromatic sharpening.

The reflected light can provide two components, in particular when measuring the skin of a person or tissue: a specular or surface reflection component, and a diffuse reflection component. When separated from each other, each component can provide useful information about the measured tissue. The surface reflection component can be useful for analysing topological characteristics of the tissue such as surface texture and visible features such as wrinkles and pores.

The diffuse reflection component, which is due to light that has interacted with the tissue interior, conveys information about the optical properties of the tissue such as the distribution of chromophores like melanin and haemoglobin but can also be used to derive topological surface information. Some photons of the incident light penetrate within the tissue and undergo multiple scattering and absorption events before some of those photons are back-scattered as diffuse reflected light. The average penetration depth of a photon is dependent on its wavelength, with longer-wavelength photons penetrating deeper into the tissue.

The blue light addresses specifically the upper skin layers including the layer with melanin. In contrast the red spectral components of the reflected light stem from deeper skin layers (hemoglobin) and are also geometrically blurred. Such unknown reflection depth results in a spatial inaccuracy concerning the reflections, in particular when utilised for deriving topological surface data like a point cloud.

By arranging a blue filter reflections from deeper skin layers can be blocked from entering the cameras and the image information provided by the monochromatic cameras is exclusively related to the (near) surface of the skin. This results in before unseen high spatial accuracy for deriving topological information, e.g. in mapping the skin surface.

Hence, the result of the combination of the monochromatic cameras and a blue filter can be point cloud data of the skin surface with very high spatial accuracy.

In an embodiment, the data acquisition functionality can be configured to provide sets of surface data, wherein the sets of surface data are acquired by capturing at least two images each with the first camera and with the second camera, and the 3D-modelling functionality can be configured to provide a set of 3D models of the object by processing the sets of surface data, wherein a number of 3D models are computed according to the number of sets of surface data acquire by one of the cameras.

In particular, the sets of surface data can be acquired by successively capturing multiple images with the first camera and with the of the second camera within a defined time period.

In particular, capturing the sets of surface data with the first camera can be synchronised with capturing the sets of surface data with the second camera. This provides surface data by two cameras which both relate to the same point in time.

In particular, the 3D-modelling functionality can be configured to generate a video sequence based on the set of 3D models.

Capturing a series of images with each of the cameras can provide to generate a video sequence which shows a series of 3D models of the object in form of a video sequence. This allows to model movement or changes (e.g. facial expression) of the object over a defined time period. Since the data base is here provided by the same cameras, the changing models fit best relative to each other and a change of the model is close to real. No simulation of any movement of changing of the object has to be computed.

In an embodiment, the 3D-modelling functionality can comprise a monitoring functionality for monitoring a state of the object. The monitoring functionality is configured to execute the data acquisition functionality at a first point in time and, by that, to provide reference surface data of the object, provide a reference 3D model of the object by processing the reference surface data and store the reference 3D model on a storage medium. Furthermore, the data acquisition functionality is executed at a second point in time and, by that, provides progress surface data of the object, a progress 3D model of the object is provided by processing the progress surface data, and stored on the storage medium. The reference 3D model is virtually aligned relative to the progress 3D model. Further, a the reference 3D model is compared with to the progress 3D model.

In particular, the monitoring functionality can comprise the step of deriving a progress measure based on the comparison of the reference 3D model with the progress 3D model, wherein the progress measure is computed by comparing volumes and/or sizes and/or shapes of the reference 3D model and the progress 3D or of a corresponding region of the reference 3D model and the progress 3D model.

In particular, the monitoring functionality can comprise the step of identifying a region of interest in the progress 3D model based on the comparison of the reference 3D model with the progress 3D mode, wherein particular progress measures are derived for particular regions of the progress 3D model and the region of interest is defined in the progress 3D model by comparing the progress measures with a defined threshold.

With such approach comparison of an appearance of the person at two timely distant points in time becomes available. Two models of the same person at two timely distant points in time can be compared with high accuracy. This allows to process the models and to identify or highlight regions in the models which have changed to an greater extent than other regions in the model. Respective changes may provide a hint for an operator (e.g. doctor) for proper assessment or to track a particular treatment of the person.

In addition, a value may be calculated based on the differences between the models which gives a measure about a global (over the entire model) or partial (over a particular region of the models) change of the object (face of a person). The measure can provide a course hint for an operator about any cosmetic effects or treatments.

In one embodiment, the measuring system can comprise a guiding functionality which is configured to provide a guiding output, in particular an acoustic guiding output and/or a visual guiding output, to guide the object (e.g. a person) to approach a defined capture position relative to the capture device, and to control or notice the execution of the data acquisition functionality as a function of a deviation of a position of the object from the capture position.

In particular, the guiding output can be derived based on image-based or video-based monitoring of the object by means of at least one camera of the set of cameras and image processing the camera data generated in the course of the monitoring.

In particular, the object can be guided to the capturing position for the first time for acquiring the reference surface data and is guided to the capturing position for the second time for acquiring the progress surface data.

Guiding the object, e.g. the person whose face should be captured, thus can be made more simple since the person receives information about any displacements or miss-alignment directly from the system. Such approach also helps for repeating several measurements with the person in identical positions relative to the capture device.

In one embodiment, the measuring system comprises a display device with a display configured to display the 3D model, in particular wherein the display device comprises the controlling and processing unit. The display device may be provided by a tablet PC, a smartphone, a notebook or the like.

In one embodiment, the capture device can comprise an infinity mirror to provide defined positioning of the object, in particular of the person, relative to the capture device. The use and advantage of an infinity mirror in combination with a capture device is described in more detail below.

The disclosure also relates to a measuring system for measuring an object, in particular the skin of a person, with a capture device which comprises a set of cameras and a set of illumination elements and a controlling and processing unit which comprises at least a data acquisition functionality which is configured to provide surface data by activating at least a part of the illumination elements for illuminating the object with measuring light and capturing at least one image by detecting measuring light reflected at the object by means of at least a part of the cameras.

In particular, the measuring system comprises a display device with a display configured to display the 3D model, in particular wherein the display device comprises the controlling and processing unit. The display device may be provided by a tablet PC, a smartphone, a notebook or the like.

The set of illumination elements comprises at least three light sources configured and arranged for illuminating the object from at least three different poses. The data acquisition functionality is configured to provide surface data by applying a shape-from-shading measurement by illuminating the object from the at least three different poses by performing at least three illumination steps with each illumination step providing illumination by one of the three light sources, capturing at least three images by capturing an image for each of the illumination steps by means of at least a first camera of the set of cameras and deriving surface topology (topography) information based on processing the at least three images and the at least three different poses of the light sources.

The first camera comprises circular polarised capture filtering and the at least three light sources comprise circular polarised illumination filtering, wherein the capture filtering and the illumination filtering provide either identical circulation directions or opposite circulation directions.

The circulation directions are preferably defined by particular arrangements of polarising filters on both sides, the illumination side and the capturing side. Filtering of identical circulation directions is provided in case the emitted circularly polarised illumination light can directly be received by the camera, i.e. the circulation direction of the measuring light has not changed. Filtering of opposite circulation directions is provided in case the emitted circularly polarised illumination light cannot directly be received by the camera, i.e. the circulation direction of the measuring light has first to be changed for proper detection.

In particular, the measuring data can be provided by performing a shape-from-shading (SFS) measurement and the surface topology information can be provided as surface normal information, in particular as a normal map or height map. Hence, the measuring data can be derived based on the SFS measurement.

A shape-from-shading (SFS) measurement can be performed by switching on one (or more) light source of the light sources at a time on and take a respective exposures with the camera during the illumination, in particular simultaneously. Then repeat this step for each light source. The sum of the acquired data is provided as SFS data. The SFS data provides high-resolution surface topology (topography) data. Alternatively, the light sources are switched on at the same time (e.g. by each of the lights using a particular wavelength different from the others) and the camera takes the exposures simultaneously. Processing of the captured image data allows to discriminate the light information for each of the light sources.

Surface normal map can be derived based on the SFS data and—after the surface normal is derived, e.g. by numerically integrating—a height map and an albedo map can be reconstructed.

The height map (SFS surface normal) can be processed together with a 3D model of above and, by that, a displacement map can be derived based thereon. The displacement map can provide a relative surface normal based on the SFS surface normal and 3D model surface normal.

The light sources can preferably be implemented to be divergent and the camera preferably has a wide-angle lens objective. Hence, the illumination and observation vectors are varying for every point on the surface of the object. To calculate the unknown surface normal accurately and quickly by solving linear equation systems, the 3D model can be exploited as input. The displacement map with higher lateral resolution and depth sensitivity can be reconstructed from the shading images. Data fusion of the displacement map and 3D data enables to resolve fine 3D details of surface (e.g. skin) structures.

The circular polarisation of the first camera and the light sources can serve to eliminate specular reflection. However, opposite circular polarisation can alternatively be applied with SFS to avoid volume scattering and to get contrast in fine detail.

In one embodiment, the set of cameras can comprise a second camera, wherein the first camera and the second camera both provide circular polarised capture filtering of the same circulation direction, or, alternatively, the first camera provides circular polarised capture filtering of a circulation direction opposite to the circulation direction of the circular polarised capture filtering of the second camera.

The data acquisition functionality can be configured to execute additionally capturing at least three images by capturing an image for each of the illumination steps with the second camera, and deriving the surface topology information based on additionally processing of the at least three images of the second camera.

Hence, the second camera can be uses to extend the measuring range or to provide a dataset to supplement the data provided by the first camera (same circulation direction). Alternatively, the second camera can be uses to acquire surface information different from the data provided by the first camera (opposite circulation direction), e.g. reflectance measurement.

In one embodiment, the first camera and the second camera can be fixedly arranged relative to each other and the optical axis of the at first camera is transversally oriented relative to the optical axis of the second camera. In particular, the optical axes enclose an angle between 80° and 100°, in particular an angle of 90°, in particular when projecting the optical axes on a plane which is defined by at least one of the optical axes and a connecting line between the first camera and the second camera.

In one embodiment, the set of illumination elements can comprise a first group of illumination elements comprising the at least three light sources and a second group of illumination elements comprising at least three further light sources configured and arranged for illuminating the object from at least three further different poses.

The first group of the illumination elements and a second group of the illumination elements both provide circular polarised illumination filtering of the same circulation direction, or alternatively, the first group of the illumination elements provide circular polarised illumination filtering of a circulation direction opposite to the circulation direction of the circular polarised illumination filtering of the second group of illumination elements.

The data acquisition functionality can be is configured to execute additionally illuminating the object from at least three further different poses by performing at least three further illumination steps with each illumination step providing illumination by one of the three further light sources, and deriving the surface topology (topography) information based on additionally processing the at least three further different poses of the at least three further light sources.

By providing further light sources and the second camera, a second optical sensor can be established which may be driven separately form the first sensor. This result in extension of the measuring range and/or in proving more accurate surface data, e.g. a denser point cloud.

In an embodiment, the at least three illumination steps and/or the at least three further illumination steps can be performed successively, in particular by providing illumination by one of the three light sources and/or by one of the three further light sources different from a light source activated before.

In an embodiment, the at least three illumination steps and/or the at least three further illumination steps can be performed simultaneously, in particular by providing illumination by the at least three light sources and/or by the at least three further light sources at the same time, in particular wherein the illumination steps are performed by providing particular illumination wavelength with each of the light sources, wherein the particular illumination wavelengths of the light sources are different from each other respectively. By that, illumination information for each of the illumination elements can be assigned to the particular light source even if the illuminations are provide at the same time.

In one embodiment, the capture device can comprise an infinity mirror to provide defined positioning of the object, in particular of the person, relative to the capture device. The use and advantage of an infinity mirror in combination with a capture device is described in more detail below.

In one embodiment the first camera, in particular the second camera, can be provided as high-resolution monochromatic cameras. The camera can comprise a filter element which is configured to transmit (only) light with a wavelength of the blue spectrum, in particular to transmit light with a wavelength out of a wavelength range between 380 nm and 500 nm, in particular between 420 nm and 480 nm, and to block transmission of light with a wavelength besides the blue spectrum, in particular to block light with a wavelength less than 380 nm and/or greater than 500 nm, in particular to block light with a wavelength out of a wavelength range between 500 nm and 1000 nm. Concerning the advantageous effect of combing a blue filter and a high-resolution monochromatic camera reference is made to the description of the respective embodiment of a measuring system above.

The disclosure also relates to a method for identifying a surface property of the skin of a person. The method comprises acquiring surface data of the skin of the person by activating illumination elements for illuminating the skin of the person with measuring light and capturing at least one image by detecting measuring light reflected (or scattered) by the skin of the person by means of a camera. A 3D model of the skin of the person is provided by processing the surface data.

Furthermore, a virtual space is provided, the 3D model is provided in the virtual space and a virtual light source is provided in the virtual space to virtually illuminate the 3D model with illumination light. Illumination parameters of the virtual light source are variable. The 3D model is virtually illuminated by applying a set of illumination parameters.

Virtually illuminating the 3D model enables to highlight or to make observable particular skin properties of the person, e.g. in a particular region of the model and/or particular skin characteristics. A user can for example vary the position of the light source relative to the 3D model and/or vary light properties like the wavelength.

It is to be understood in context of the present disclosure that the approach of virtually illuminating the 3D model can be applied with any 3D model generated with any measuring system described herein. The other way around, any approach concerning the modelling or data acquisition of any embodiment of the method can correspondingly be applied with each measuring system described.

In an embodiment, the 3D model can be provided by deriving a point cloud based on the surface data, e.g. based on a photogrammetric measurement or shape-from-shading measurement. A 3D mesh is generated based on the point cloud, in particular a textured 3D mesh and a set of landmarks is identified in the 3D mesh. Further, a base template of the skin of the person to be modelled is provided, the 3D model is provided by fusing the 3D mesh and the base template utilising the landmarks, wherein the number of meshes of the 3D mesh is maintained in the course of fusion, and texturing of the 3D model with at least (micro-) normal texturing data and/or displacement data related to the skin of the person is applied.

In particular, the (micro-)normal texturing data is derived based on a specular map or based on data derived with a measuring system according to above, in particular data derived by shape-from-shading.

In one embodiment, the specular map can be derived by illuminating the object and capturing at least one diffuse image, wherein illuminating and capturing provide filtering of identical circular or linear polarisation directions, illuminating the object and capturing at least one reflection image, wherein illuminating and capturing provide filtering of opposite circular or linear polarisation directions, comparing the image data of the at least one diffuse image and the image data of the at least one reflection image, and deriving the specular map based on the comparison of the image data.

By texturing the 3D model with (micro-)normal texturing data, e.g. a normal map of the skin of the person, the 3D model comprises topological information on a fine scale which also comprises topographic shapes, extensions and/or sizes of particular skin properties like wrinkles. Such normal texturing hence allows to calculate an interaction of the virtual illumination light with the skin on a fine level and, thus, also to compute the effect on the virtually impinging illumination light. By that, small structures of the skin can be made observable by suitably adjusted illumination.

Furthermore, (micro-)normal texturing data can comprise displacement data, e.g. a displacement map. Displacement mapping has the advantage that the geometry of the object is actually changed. That is, if one looks at a surface of the 3D model up close at a shallow angle, its structure still remains visible. In contrast, surfaces viewed by other methods can appear absolutely planar as soon as they are viewed from a steep angle. Under the influence of light sources and shadows, structures created with displacement mapping appear more realistic because the changed geometry also affects the illumination.

Processing a displacement map can comprise displacing the points of the grid (vertices) of the 3D model according to the texture (height) information along their normals, i.e. perpendicular to the surface. For example, a height relief can be transferred to a flat (planar) surface by applying a displacement map, thus giving it a rough texture.

In an embodiment, the method provides virtually illuminating the 3D model by illuminating of wrinkles by selecting or defining a wrinkle region in the 3D model which comprises at least one wrinkle, defining a predominant direction which represents a predominant extension of the at least one wrinkle and computing a region normal which represents a normal direction related to the wrinkle region, in particular wherein the region normal corresponds to a normal vector in the centre of the wrinkle region.

The illuminating of wrinkles further can comprise orienting an illumination axis perpendicular to the predominant direction and the illumination axis enclosing an illumination angle with the region normal, in particular wherein the illumination axis intersects the region normal, and providing the virtual light source on the illumination axis.

The particular illumination provides reliable illumination of the at least one wrinkle so that it can be observed in an improved quality. The wrinkle is illuminated so that at least one side wall of the wrinkle provides direct line of sight to the virtual illumination source and thus is directly illuminated. The opposite side wall causes a shadow which is generated accordingly. Such effects make the wrinkle visually observable.

In particular the predominant direction can be defined by selecting a direction according to a pre-known wrinkle appearance in the wrinkle region (e.g. by an operator of automatically based on surface data or topology/topographic data), or by applying a wrinkle analysis to the 3D model according to the wrinkle region. The wrinkle analysis may be implemented as or based on an algorithm which makes use of artificial intelligence.

In one embodiment, the region normal can be derived based on averaging a number of normal vectors related to the wrinkle region. As for example, a normal vector for each mesh inside the region can be considered and the region normal can be computed based on the normal vectors of the meshes.

In an embodiment, the illumination angle is greater than 45° and/or the illumination angle is smaller than 60°. The angle can be respectively varied for providing best observation of the wrinkle. The optimised angle can depend on the shape of the wrinkle, in particular on the slope (gradient) of at least one of the side walls.

In particular, a setting functionality for setting the illumination angle can be provided upon execution of which an interface, in particular a UI (user interface), is provided to variate the illumination angle between 45° and 60° upon an input of an operator. Hence, the operator is enabled to adjust the illumination angle to further improve the appearance of the wrinkle.

In one embodiment an optical axis of the virtual light source can be aligned coaxial with the illumination axis.

In one embodiment the method can comprise showing, depicting and/or capturing of the wrinkles by selecting or defining a viewing direction which is diametrically opposed to the region normal, the viewing direction providing generating a wrinkle image according to an optical axis parallel or coaxial to the viewing direction and facing the wrinkle region, and generating and/or providing a wrinkle image according to the viewing direction. For generating and/or providing the wrinkle image a camera can be virtually arranged according to the viewing direction and the image can be taken by the virtual camera. In particular, the wrinkle image can be computed by processing the boundary conditions given with the set viewing direction.

In one embodiment the virtual light source can be is provided by a point light source, by an elongated light source, in particular wherein the extension direction of which is parallel to the predominant direction, and/or by micro-illumination, wherein for each pixel or mesh an incidence angle is calculated based on an extension of the wrinkle or based on the illumination angle or based on a normal vector for the pixel or mesh.

In case of using micro-illumination, instead of calculating a region normal for the region respective local normal vectors can be calculated for providing proper alignment of the illumination of each pixel.

Setting a particular light source can improve observation of particular wrinkle structures.

In one embodiment, the 3D model can represent a face of the person, the face defining a front side, and the virtual light source is virtually oriented so that an illumination direction is directed towards the 3D model and the virtual light source is virtually positioned according to one of the following positions:
- on the front side of the face with a defined distance offset relative to the 3D model,
- above and in the front area of the face with a defined distance offset relative to the 3D model,
- lateral and in the front area of the face with a defined distance offset relative to the 3D model, or
- below and in the front area of the face with a defined distance offset relative to the 3D model.

In one embodiment, an appearing state of the 3D model is determined based on the virtual illumination, and the surface property of the skin of the person is derived based on the appearing state, wherein determining the appearing state of the 3D model comprises computing an interaction of the virtual illumination of the 3D model and the micro-normal texturing data.

In particular, a measure related to the appearing state can be derived. The measure provides information about the surface property, in particular about an amount, density or size of a particular skin structure like wrinkles or pores.

In one embodiment, a first illumination of the 3D model can be applied by applying a first set of illumination parameters and a first appearing state of the 3D model is determined based on the first virtual illumination, a second illumination of the 3D model can be applied by applying a second set of illumination parameters and a second appearing state of the 3D model is determined based on the second virtual illumination, and a particular surface property of the skin of the person can be identified based on comparing the first appearing state and the second appearing state.

In particular, a particular region in the model is identified based on the identified particular surface property and a marker is provided with the 3D model to mark the particular region. Hence, by varying the illumination an observed skin structure can be identified and highlighted or marked.

In one embodiment the illumination parameters can comprise at least one of:
- a relative position of the 3D model and the virtual light source,
- a wavelength of the illumination light,
- a property of the illumination light, in particular regarding diffused or collimated light, and/or
- a polarisation state of the illumination light.

The disclosure also relates to a computer program product comprising program code for performing the method of above. The computer program product can comprise a corresponding algorithm to execute the method. The computer program product can be executed on a computer or on a controlling and processing unit of a measuring system mentioned above.

The disclosure also relates to an approach for providing proper and suitable alignment of the person relative to a capture device. By that approach, the positioning and orientation of the person can be provided in very accurate manner. Moreover, the person can be situated relative to the device repeatedly, i.e. the person can be placed in front of the device so that suitable measurement of the person can be performed, wherein such measurement can be repeated for several times wherein the person is oriented and placed basically in same manner relative to the device.

The related idea is to provide an infinity mirror at a capture device. The infinity mirror is arranged and oriented so that a person to be measured can orientate relative to the device by looking inside the infinity mirror. The positioning and orientation of the person relative to the device is as desired in case the person can observe a defined appearance inside of the infinity mirror. By that, repeated positioning and orientation of the person relative to the device can be provided as well.

The infinity mirror is preferably arranged and oriented so that a desired insight axis of the mirror is in the centre of the capture device.

In one embodiment the insight axis of the infinity mirror is aligned to be an angle bisector of an angel enclosed by the optical axes of a first camera and a second camera of the device. The angle can be defined by projecting the optical axes on a plane which is defined by at least one of the optical axes and a connecting line between the first camera and the second camera.

Therefore, the disclosure relates to a capture device for imaging a person, in particular the face or a part of the face of the person. In one embodiment, the capture device can be embodied for measuring the skin of a person, in particular according to a capture device described above. The capture device comprises at least one camera for capturing an image of the person.

The capture device comprises an infinity mirror which comprises at least two mirror surfaces arranged oppositely (apart) from each other, a light source for emitting light, and a front side to look inside the infinity mirror. The infinity mirror is arranged at the capture device and placed and oriented relative to the capture device so that a capture range with an insight axis and an insight distance for the person is defined and so that defined capturing of the person by means of the at least one camera is provided when the person is positioned according to the capture range. This can provide for suitable and repeatable capturing of the person by defined looking inside the infinity mirror.

In particular, the capture device comprises a first and a second camera which are configured and designed to capture images of the person and which provide image data for generating at least a geometric model of the person. The cameras can be arranged and configured according to any one of the embodiments described above.

The camera of the capture device can, for example, be provided by a sensor arrangement of a particular measuring or sensing system. As for example, the camera may be represented by an image sensor or any other kind of detecting sensor. Hence, the camera can provide at least a part of a ToF (time-of-flight) sensor, a depth sensor, a stereo imaging device or the like. In particular, the capture device can provide means to compute a 3D pose.

The capture range can be defined as a region of particular distance and direction away from the capture device. The camera can provide an optical setup which provides suitable image capturing of objects or persons which are present in the capture range. Hence, the insight axis can define a direction and the insight distance can define a position of e.g. a centre point of the capture range. The capture range can be provided by a spherical area around the centre point.

In one embodiment, a defined inner appearance of the inside of the infinity mirror can be associated with the capture range. The infinity mirror can be arranged at the capture device and placed and oriented relative to the capture device so that guiding of the person can be provided by looking inside the infinity mirror and simultaneously adjusting the relative position of the person until the defined inner appearance is observed by the person. Accurately positioning of the person is provided when the person is positioned according to the capture range.

In an embodiment, the insight axis can be defined by a surface of at least one of the two mirror surfaces, in particular the insight axis is perpendicular to and intersects a centre point of the surface of the at least one of the two mirror surfaces. In particular, the insight axis is equally distant for the first and the second camera.

In one embodiment, the insight distance can be defined by the configuration of the infinity mirror, in particular by the relative arrangement of the at least two mirror surfaces and the light source.

In an embodiment, the infinity mirror can provide an inner appearance which appears to be a tunnel tapering in infinity and can provide required aligning for the person relative to the capturing unit when the inner appearance is entirely observable by the person, in particular when all sides of the tunnel are observable.

A particular configuration of the infinity mirror provides a defined inner appearance of the infinity mirror and further determines under which angle and in which distance one has to look inside the mirror for being able to totally observe e.g. an inner pattern. Hence, the capture range or position can be determined according to this inner appearance of the infinity mirror.

In an embodiment, the infinity mirror, in particular the inner appearance of the infinity mirror, can provide avoiding of squinting of the person in the course of capturing an image of the person, e.g. for providing surface data related to the skin or the face of the person. This effect can be provided by an inner appearance which leads the person to look into infinity, e.g. an endless tunnel. Hence, advantageously, capturing of an image of the person can be provided without any squinting of the person.

In an embodiment, the infinity mirror, in particular the inner appearance, can provide to capture the person with low distance between the person and the capture device and without squinting of the person. For that, the infinity mirror can be designed so that the insight distance results to be comparatively short and the person has to approach the device comparatively close to see the inner structure of the infinity mirror.

By providing a short insight distance the measuring of the person can be provided in an advantageous manner since the face of the person can be captured with great detail and/or from all sides of interest and with high accuracy.

In an embodiment, at least one of the mirror surfaces can be built semi-transparent and is arranged on the front side.

In one embodiment, the infinity mirror can comprise the front side and an infinity side, wherein the front side is arranged opposite apart of the infinity side and at least one of the mirror surfaces is built reflective and is arrange on the infinity side. In particular wherein the front side and an infinity side are connected by side walls.

In particular, the mirror surfaces can be provided by two separate mirrors being arranged opposite to each other. Alternatively, the mirror surfaces can be provided by two boundary surfaces of an optical element, e.g. the front side and the back side of a single element. As for example, the front side and the back side of a glass element can be coated, one reflective the other one and semi-reflective, and the mirror surfaces are provided by the coated sides.

In one embodiment, the light source is arranged between or in front of the mirror surfaces, in particular in front of the front side. In particular, the light source can be arranged closer to the front side than to the infinity side.

In one embodiment, the light source can be provided by a number of LEDs which are circumferentially arranged around the centre of the infinity mirror, in particular along the perimeter of the infinity mirror. Such arrangement of LEDs can provide the effect of observing a tunnel inside of the infinity mirror which tappers to infinity.

The disclosure also relates to a measuring system for measuring the skin of a person. The measuring system comprises a capture device with an infinity mirror of above and a controlling and processing unit. The controlling and processing unit comprises at least a data acquisition functionality which is configured to provide surface data by capturing at least one image by detecting the skin by means of the at least one camera, in particular by the first and/or the second camera. As for example, the surface data can be image data or a point cloud derived from the image data. The controlling and processing unit comprises a 3D-modelling functionality which is configured to provide a 3D model of the skin by processing the surface data.

The system can in particular comprise a display device having a display and being configured to display the 3D model on the display.

In one embodiment, the capture device can comprises at least one illumination element for illuminating the skin with measuring light and the data acquisition functionality can be configured to activate at least a part of the illumination elements for illuminating the skin and for capturing the at least one image during illumination.

In one embodiment, the controlling and processing unit can comprise a guiding functionality which is configured to provide a guiding output, in particular an acoustic guiding output and/or a visual guiding output, to guide the person to approach the defined capture range relative to the capture device, and control or notice the execution of the data acquisition functionality as a function of a deviation of a position of the object from the capture range.

In particular, the guiding output is derived based on image-based or video-based monitoring of the person by means of at least one camera of the set of cameras and image processing the camera data generated in the course of the monitoring.

Such functionality provides advantageous, fast and repeatable positioning of the person relative to the capture device.

The disclosure also relates to a guiding device for accurately positioning a person, in particular the face or a part of the face of the person, relative to the guiding device. The guiding device comprises a camera for capturing an image of the person, and a controlling and processing unit.

The guiding device comprises an infinity mirror with at least two reflective surfaces arranged oppositely (apart) from each other, a light source for emitting light, and a front side to look inside the infinity mirror.

In particular, the mirror surfaces can be provided by two separate mirrors being arranged opposite to each other. Alternatively, the mirror surfaces can be provided by two boundary surfaces of an optical element, e.g. the front side and the back side of a single element. As for example, the front side and the back side of a glass element can be coated, one reflective the other one and semi-reflective, and the mirror surfaces are provided by the coated sides.

The infinity mirror is arranged at the guiding device and placed and oriented relative to the guiding device so that a capture range with an insight axis and an insight distance range for the person is defined, wherein a defined appearance of the inside of the infinity mirror is associated with the capture range. Moreover, the infinity mirror is arranged at the guiding device and placed and oriented relative to the guiding device so that guiding of the person is provided by looking inside the infinity mirror and simultaneously adjusting the relative position of the person until the defined appearance is observed by the person. By that, accurately positioning of the person is provided when the person is positioned according to the capture range.

The controlling and processing unit comprises a guiding functionality which is configured to derive a guiding output based on image-based or video-based monitoring of the person by means of the camera and process the camera data generated in the course of the monitoring, and is configured to provide the guiding output, in particular an acoustic guiding output and/or a visual guiding output, to guide the person to approach the defined capture range relative to the guiding device.

Therefore, the guiding device can provide positioning of a person in front of the device in defined and comparatively accurate manner. The person is enabled to self-align relative to the device by help of the infinity mirror, i.e. by looking into the mirror and rearrange his/her position and/or orientation (iteratively) as long as the inside of the infinity mirror appears to the person in nominal state.

It should be understood that the embodiments of above related to measuring systems, capture devices and methods for identifying a surface property can be combined among each other and should not be understood as providing isolated, separated or non-combinable embodiments.

BRIEF DESCRIPTION OF THE DRAWINGS

By way of example only, aspects will be described more fully hereinafter with reference to the accompanying figures, wherein.

DETAILED DESCRIPTION

Figure 1:
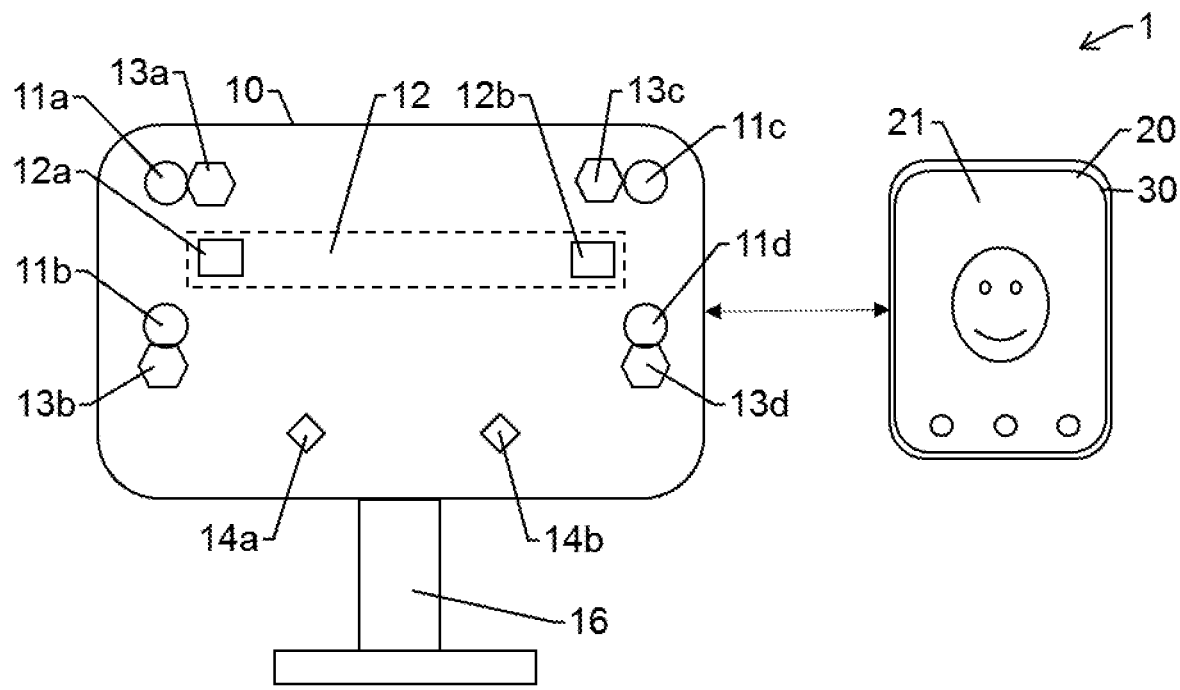
FIG. 1 shows an embodiment of a measuring system.

FIG. 1 shows an embodiment of a measuring system 1. The measuring system comprises a capture device 10 and a display device 20. A controlling and processing unit 30 is part of the display device 20.

The display device 20 may be embodied as a tablet or other hand-held computing device having a display 21 to display data, in particular a 3D model computed based on the data acquired with the capture device 10. The display device 20 can be connected to the capture device 10 by wireless communication means, e.g. by Bluetooth WiFi or the like. It is to be understood that the communication preferably is provided for transferring surface data from the capture device 10 to the display device 20. Data processing, including generation of a 3D model, can at least mainly be performed on side of the processing unit at the display device 20.

The controlling and processing unit is configured to control the data acquisition with the capture device 10. For that, the controlling unit may comprise a sub-unit which is arranged on side of the capture device 10. For data acquisition the controlling unit controls activating at least a part of the illumination elements of the capture device 10 for illuminating the object with measuring light and capturing at least one image by detecting measuring light reflected at the object by means of at least a part of the cameras. The controlling and processing unit may comprise a respective (algorithmic) data acquisition functionality to provide the measurement.

The object to be measure preferably is the skin of a person, more preferably the face of the person.

Based on the at least one captured image respective surface data can be provided. The surface data may be in form of raw image data or in form of a point cloud which can be processed based on the captured image.

The controlling and processing unit 30 is further configured to provide a 3D model of the object by processing the surface data. The controlling and processing unit 30 may therefore comprise a 3D-modelling functionality.

In one embodiment, the controlling and processing unit 30 is configured to derive a point cloud based on the surface data and to generate a 3D mesh based on the point cloud, in particular a textured 3D mesh. A set of landmarks can be identified in the 3D mesh and a (standardized) base template of the skin of the person to be modelled can be provided. Based on that, the 3D model can be computed by fusing the 3D mesh and the base template utilizing the landmarks, wherein the number of meshes of the 3D mesh is maintained. Additionally, at least texturing of the 3D model can be applied with micro-normal texturing data related to the skin of the person, wherein the micro-normal texturing data can be derived based on a specular map.

The capture device 10 comprises a first group of the illumination elements 11a-11d which each comprises circular polarised filtering of a first circulation direction. Hence, the illumination elements 11a-11d are configured to emit polarised measuring light having a first circulation polarising direction.

Furthermore, the capture device 10 comprises a first group of the cameras 12. The first group of the cameras 12 comprises at least a first 12a and a second camera 12b. Each of the cameras 12a,12b comprises circular polarised filtering of the first circulation direction.

Circular polarised filtering can be provided by use of a combination of a linear polarising filter and a quarter-wave ($\lambda/4$) plate. Both components can be arranged in front of the light source to provide the illumination elements 11a-11d emitting circularly polarised light.

The input light going into the linear polariser filter is known as being randomly polarised (unpolarised). The light exiting the linear polariser filter is linearly polarised light. The quarter-wave plate typically has what is called a fast axis and a slow axis which are perpendicular to each other. To create circularly polarised light (as opposed to elliptically polarised light), the polarising axis (of the linear polariser filter) must be at 45° to the fast and slow axis. Thus the relative 45° polariser axis allows the electromagnetic fields to be parallel to the fast and slow axis of the wave plate. The polarised light then exits the quarter-wave plate, with either the Ex or Ey field (components of the electric field in x- and y-axis) shifted by a quarter of a wave.

As a result concerning time, the Ex and Ey electric fields, and the polarising axis that is a vector of the two electric fields, the light that exits the back of the circular polarising filter will have a polarisation state rotating. The part of the electric field (Ex or Ey) that is parallel to the wave plate's slow axis will determine which field is shifted and thus which way the polariser axis rotates, either clockwise (right-handed) or counter clockwise (left-handed). Hence, by relative orientation of the linear polarised filter and the quarter-wave plate the circulation direction can be set, e.g. when rotating the linear polarised filter by 90°, the circulation direction changes.

If the orientation of the polarising filter does not exactly correspond to one of the angle bisectors of the x-y-plane (45° to the fast and slow axis), the result is not circular polarisation but may be elliptical polarisation. However, in context of the present disclosure circular polarised filtering should be understood to also include light of elliptical polarisation.

The principle of above also can be used on side of the cameras 12a and 12b. If circularly polarised light falls on a λ/4 plate, linearly polarised light is produced. Hence, each of the cameras 12a,12b comprises circular polarised filtering which comprises a λ/4 plate and a linear polarisation filter. The circular polarised filtering of the cameras is configured to provide detection of light which is circularly polarised according to the first circulation direction. In particular, the linear polarisation resulting from passing circularly polarised light of the first circulation direction through a λ/4 plate comprises an orientation which is perpendicular (shifted by 90°) to the linear polarisation of the light passing a λ/4 plate to generate the circular polarisation of the first circulation direction.

Hence, the approach of above may also be considered to provide a detection of light (polarised filtering of a first orientation) being cross polarised relative to the emitted light (polarised filtering of a second orientation orthogonal to the first orientation).

The arrangement of the illumination devices 11a-11d and the cameras 12a-12b provides to detect diffuse scattering of the measuring light at the surface to be measured. In particular, the setup can provide to eliminate specular reflection.

The handedness (circular polarisation direction) of polarised light is reversed reflected off a surface at normal incidence. Upon such reflection, the rotation of the plane of polarisation of the reflected light is identical to that of the incident field. However, with propagation now in the opposite direction, the same rotation direction that would be described as "right-handed" for the incident beam, is "left-handed" for propagation in the reverse direction, and vice versa.

Change of handedness holds strictly for light reflected at normal incidence. For instance, right circularly polarised light reflected from a dielectric surface at grazing incidence will still emerge as right-handed polarised.

In case the circular polarisation direction is changed upon reflection at the surface, the resulting polarisation direction after passing the quarter wave plate at the camera is shifted correspondingly by 90°. In such case, the reflected measuring light will not be detectable by the camera having the same polarisation filtering as the illumination unit.

Hence, due to the effect of change of circular polarisation direction when the measuring light is reflected, eliminating or avoiding of detecting of specular reflection can be provided and diffusely scatted light can still be detected.

An advantage of using circularly polarised measuring light is that image information of the whole object (e.g. face of a person) can be determined, while if using linearly polarised light only some areas will be detected due to more strict polarisation limitations.

The capture device 10 also comprises a second group of the illumination elements 13a-13d. These illumination elements 13a-13d comprises circular polarised filtering of a second circulation direction, opposite to the first circulation direction. As for example, the first group of illumination elements 11a-11d emit light with "right-handed" circular polarisation and the second group of illumination elements 13a-13d emit light with "left-handed" circular polarisation.

Since the camera group 12 comprises one fixed polarisation direction (opposite to the circulation direction of the second group of illumination elements), the light emitted by the second group of the illumination elements 13a-13d is detected on side of the cameras 12a and 12b in case of reflection at the surface. Hence, such setup provides detection of reflective regions a the surface. The linear polarisation direction of the measuring light reaching the camera sensor is the same as of the linearly polarised light used for generating the circularly polarised light.

The capture device 10 further comprises a second group of cameras 14a and 14b. The second group provides to acquire extended information about the object. In the present embodiment, the cameras 14a and 14b comprise the same polarisation filtering as the first group 12. According to an alternative embodiment, the, the cameras 14a and 14b comprise the opposite polarisation filtering as the first group 12. Such embodiment may also comprise illumination elements which all comprise polarisation filtering of one direction.

The second group of cameras 14a and 14b may preferably provide acquisition of image data for generating texture maps for the 3D model, e.g. an albedo map and/or a specular map. The albedo map can be derived by detecting diffuse light scattering (same polarising filtering) while the specular map can be derived by detecting reflections (opposite polarising filtering). The specular map can preferably be derived by comparing diffuse and reflection polarisation shots.

Further, a normal map can be derived by processing the specular map. A displacement map may be derived based on the normal map.

With the embodiment of FIG. 1 the face of a person can be measured with high precision. A 3D model of the face can be generated. For that, the first group of illumination elements 11a-11d are activated to emit circularly polarised measuring light of the first circulation direction. The first group of cameras 12a-12b is activated, in particular synchronised with activating the illumination elements 11a-11d, and the surface data is provided. The surface data, i.e. in form of a point cloud, can be processed by means of photogrammetric processing of the image date, e.g. by also processing known positions and orientations of the cameras 12a-12b and/or the light sources.

An initial 3D model can be generated to preferably provide the geometry of the face of the person. The initial 3D model is further processed and/or merged with texture data to provide a textured, final 3D model. E.g. the initial 3D model is processed together with the albedo map, the specular map, the displacement map and the normal map.

The present embodiment is designed as a portable multi camera device which provides improved flexibility concerning portability and handling by a user. For that, the device 10 comprises a pedestal 16 to place the device 10 on a table or the like. The device 10 can be carried by an operator, in particular by a health professional, to enable measuring the skin of a patient e.g. at different locations.

Figure 2A:
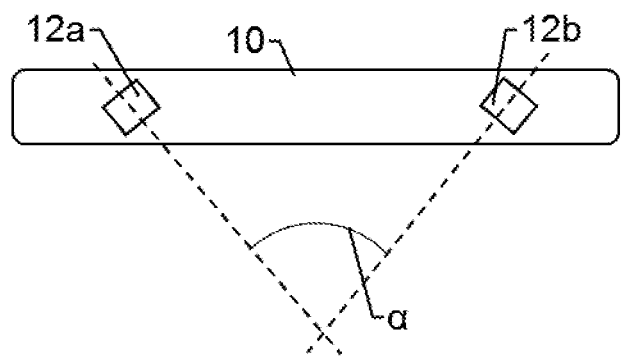
FIGS. 2a and 2b show an embodiment of a measuring system.

FIG. 2a shows an embodiment of a capture device 10. FIG. 2a shows a crosscut of the capture device 10 in a top view direction. The capture device 10 comprises two cameras 12a and 12b which are arranged fixed relative to each other. The optical axis of the first camera 12a is transversally oriented (tilted) relative to the optical axis of the second camera 12b.

The optical axes of the first camera 12a and the second camera 12b preferably enclose an angle α between 80° and 100°, here angle α of 90°. The angle α can be determined by projecting the optical axes on a plane which is defined by at least one of the optical axes and a connecting line between the first camera 12a and the second camera 12b.

By such arrangement all parts of the face and also of the neck can be covered by the cameras 12a and 12b.

The cameras 12a and 12b are configured as high resolution cameras. An advantage of such an embodiment is that a high density (resolution) of surface data can be provide which results in a correspondingly high precise geometric 3D model. Texturing of the geometric model is provided by uses of data which is provided by further camera, e.g. like 14a and 14 of FIG. 1.

In one embodiment the data acquisition functionality is configured to provide sets of surface data, wherein the sets of surface data are acquired by capturing at least two images each with the first camera and with the second camera. The images of one camera are capture one after the other having a defined time delay. One of the sets of surface data is based to data which is acquired with the first and the second camera at one instance in time. Hence, capturing the sets of surface data with the first camera is synchronised with capturing the sets of surface data with the second camera.

In other words, each set of surface data provides a state of the object (face) to be measured at a different point in time. The processing unit is further configured to provide a set of 3D models of the object by processing the sets of surface data, wherein a number of 3D models are computed according to the number of sets of surface data acquire by one of the cameras. As a result a series of 3D models can be generated. Based therein, a video sequence can be generated which is capable of showing changes or movements of the face.

Figure 2B:
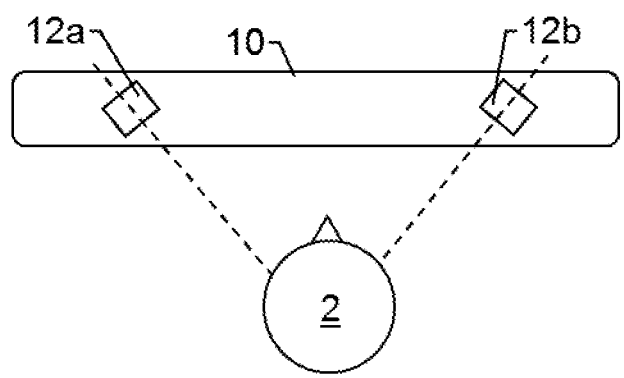

FIG. 2b shows a crosscut of the capture device 10 and a person 2 (object) to be captured in a top view direction. As can be seen, by the particular arrangement of the optical axes of the cameras 12a and 12b, the face of the person 2 can be captured from two direction in a way so that the face can entirely be covered by the generated image data. In particular, the entire region of interest e.g. for facial cosmetic treatment can be covered, e.g. the front side, left and right face half and neck.

Figure 3:
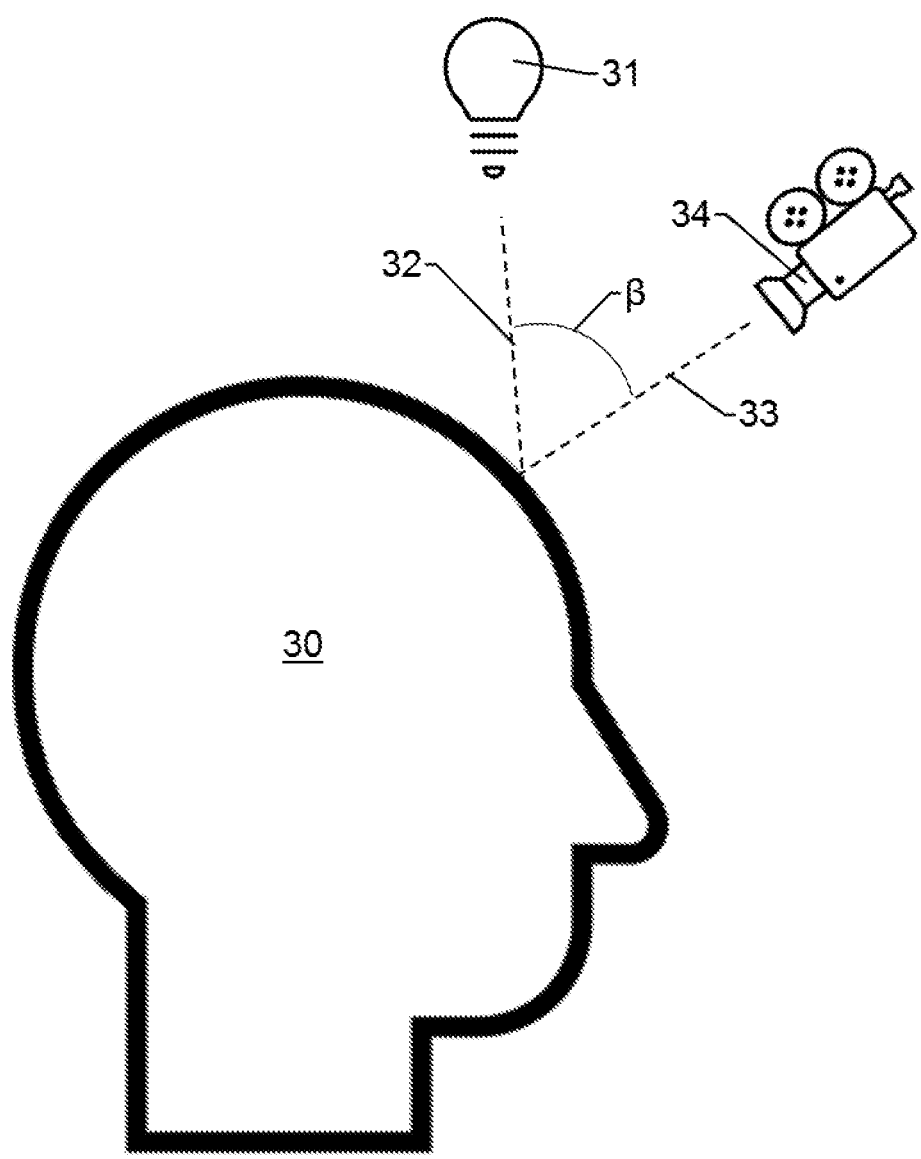
FIG. 3 shows an embodiment of virtual illumination.

FIG. 3 shows an embodiment which is related to virtual illumination of a 3D model 30 of the face of a person. The approach of virtual illumination is directed to identifying a surface property of the skin of the person. For that, the 3D model is derived by activating illumination elements for illuminating the skin of the person with measuring light, capturing at least one image by detecting measuring light reflected by the skin of the person by means of a camera and processing the surface data. The 3D model may be derived by means of any one of the systems or devices mentioned or described above.

The 3D model is provided in a virtual space which allows to freely align and orientate the model. In addition, a virtual light source 31 is provided in the virtual space to virtually illuminate the 3D model with illumination light 32, wherein illumination parameters of the virtual light source are variable. Illumination can be provided by applying a defined set of illumination parameters, e.g. defined wavelength and/or polarisation. A virtual interaction of the emitted illumination light 32 and the 3D model 30 can be calculated and provided, e.g. by displaying the illuminated model.

In one embodiment, specific illumination of the model can be provided to particularly identify of highlighting wrinkles. There may be chosen to provide global illumination of the (almost) the entire face or to provide partial illumination of a selected wrinkle region of the model which comprises at least one wrinkle, preferably a number of wrinkles.

The wrinkle provides or extends in one predominant wrinkle direction. Such predominant wrinkle direction can be selected according to a pre-known wrinkle appearance in the wrinkle region of can be defined by applying a wrinkle analysis algorithm to the 3D model according to the wrinkle region. The algorithm may preferably at least be supported by artificial intelligence.

Based on the region to be illuminated, region normal (vector) 33 can be calculated which represents a normal direction related to the wrinkle region, in particular wherein the region normal 33 corresponds to a normal vector in the centre of the wrinkle region. The region normal vector can be derived based on an averaging of a number of normal vectors related to the wrinkle region, in particular by averaging the normal of each mesh in the region.

The illumination axis 32 is then oriented perpendicular to the predominant direction and such that an illumination angle β with the region normal 33 is enclosed. The illumination axis 32 intersects the region normal 33 at the surface of the 3D model.

The virtual light source 31 is accordingly provided along the illumination axis 32, e.g. the optical axis of the light source is coaxial with the illumination axis 32. The virtual light source 31 can be provided as a point light source, as an elongated light source, in particular wherein the extension direction of which is parallel to the predominant direction, or as a micro-illumination, wherein for each pixel an incidence angle is calculated based on an extension of the wrinkle or based on the illumination angle or a normal vector for the pixel.

With such configuration the light emitted by the source 31 illuminates at least one side wall of the wrinkle and provides advantageous appearance of the wrinkle on a display.

The illumination angle β is preferably be chosen to be I a range between 45° and 60°. The illumination angle β can be varied by a user, e.g. using an UUMMI on a display showing the illuminated model. By that, the operator can vary the illumination direction to provide an optimized view of the model.

As can be seen, the viewing direction for presenting the illuminated model is set to be parallel to the normal 33. A virtual camera 34 is shown accordingly. This provides generating a wrinkle image according to an optical axis parallel or coaxial to the viewing direction and facing the wrinkle region.

Figure 4:
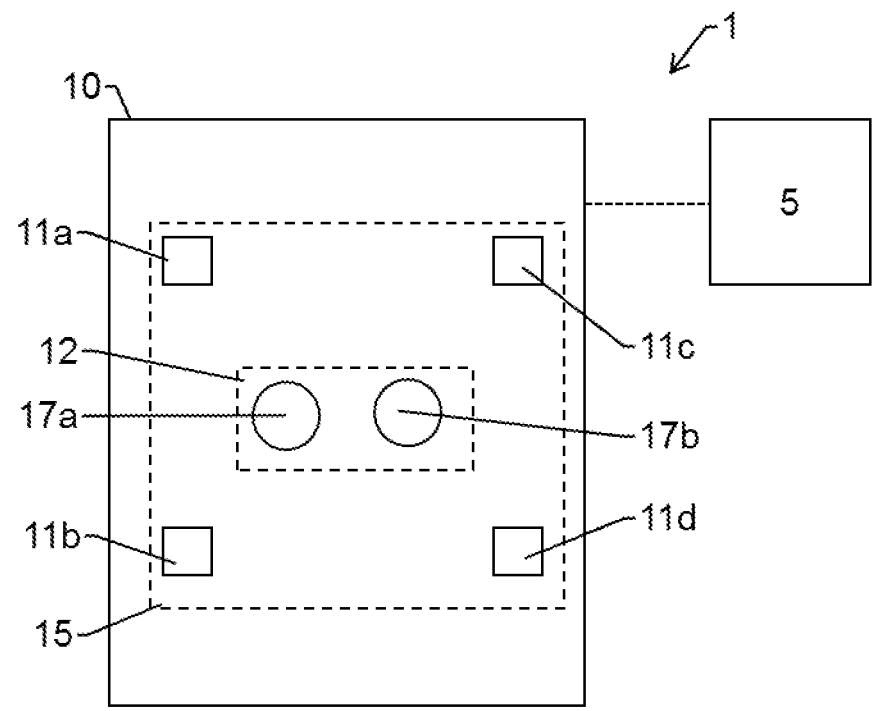
FIG. 4 shows an embodiment of a measuring system.

FIG. 4 shows an embodiment of a measuring system 1. The measuring system comprises a capturing device 10 and a controlling and processing unit 5.

In the shown embodiment, the measuring device comprises two cameras 17a and 17b and four illumination elements 11a-11d. The cameras and illumination elements provide a first optical sensor 15 and a second optical sensor 30. The first optical sensor 20 provides a first field of view and is configured for collecting first measuring data representing at least a first part of the object, e.g. of a face of a person.

The first optical sensor 15 is implemented as a shape-from shading (SFS) sensor, wherein the cameras 17a,17b are also part of the SFS sensor 15.

For providing measuring (surface) data, at least one of the cameras 17a,17b is controlled to capture image data synchronised with illumination devices 11a-11d. For that, the controlling and processing unit 5 comprises a capturing mode (data acquisition functionality) which is configured to provide the surface data by illuminating the object from four different poses by performing at least four successive illumination steps with each illumination step providing activating one of the four light sources 11a-11d. At least four images are captured by capturing an image for each of the successive illumination steps. Surface topology information is derived based on processing the at least four images and the four different poses of the light sources 11a-11d. In an alternative embodiment, illuminating and image capturing can be performed simultaneously.

It should be understood that according to an alternative embodiment, the capturing device 10 is embodied to comprise only one of the cameras 17a, 17b and surface data is acquired by capturing the images by the only one camera.

The two cameras 17a,17b comprise circular polarised capture filtering and the four light sources 11a-11d comprise circular polarised illumination filtering, wherein the capture filtering and the illumination filtering provide either identical circulation directions or opposite circulation directions.

The first camera 17a and the second camera 17b both provide circular polarised capture filtering of the same circulation direction. In an alternative embodiment, the first camera 17a provides circular polarised capture filtering of a circulation direction opposite to the circulation direction of the circular polarised capture filtering of the second camera 17b.

As described above, depending on the polarisation configuration the device is preferably capable of providing diffuse image data or reflection image data of the object. By providing different polarisation directions with the cameras 17a and 17b the device is capable to provide both diffuse image data and reflective image data.

The first camera 17a and the second camera 17b are fixedly arranged relative to each other and the optical axis of the at first camera 17a is transversally oriented relative to the optical axis of the second camera 17b. The optical axes enclose an angle between 80° and 100°, in particular 90°, in particular when projecting the optical axes on a plane which is defined by at least one of the optical axes and a connecting line between the first camera 17a and the second camera 17b.

The four illumination steps are performed successively, in particular by providing illumination by one of the four light sources different from a light source activated before. Alternatively, the four illumination steps are performed simultaneously, wherein each light source 11a-11d emits measuring light of a particular wavelength different from the wavelengths of the remaining three light sources. By that, portions of captured image data can be assigned to the respective illumination source.

Figure 5:
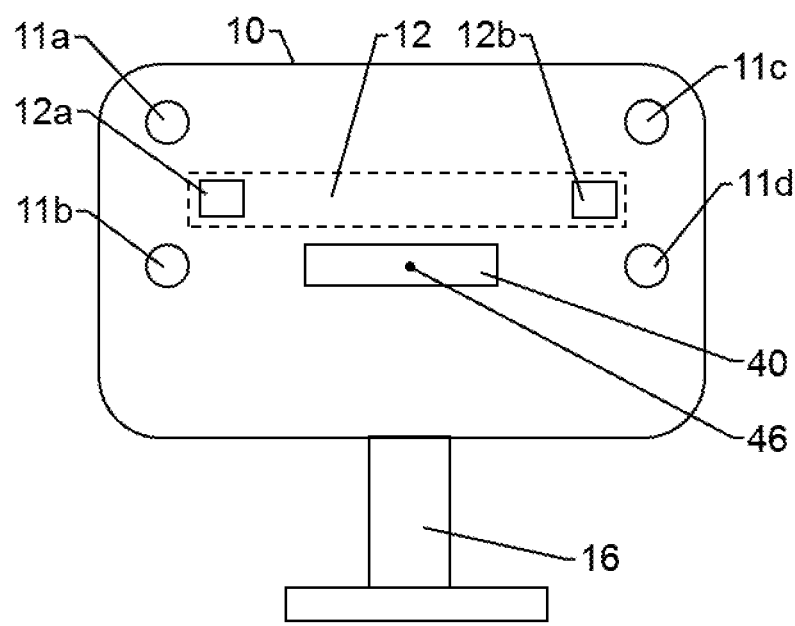
FIG. 5 shows an embodiment of a capturing device.

FIG. 5 shows an embodiment of a capture device 10. The capture device 10 is configured to measure the skin of a person, in particular the face of a person.

The capture device 10 comprises a set of illumination elements 11a-11d for illuminating the skin with measuring light and a set of cameras 12a and 12b for capturing an image of the skin by detecting at least a part of the measuring light which is reflected at the skin. The capture device 10 also comprises a pedestal to place the device 10 on a table or desk to provide flexible measuring conditions. E.g. The height of the stand can be fixed or adjustable.

Figure 6:
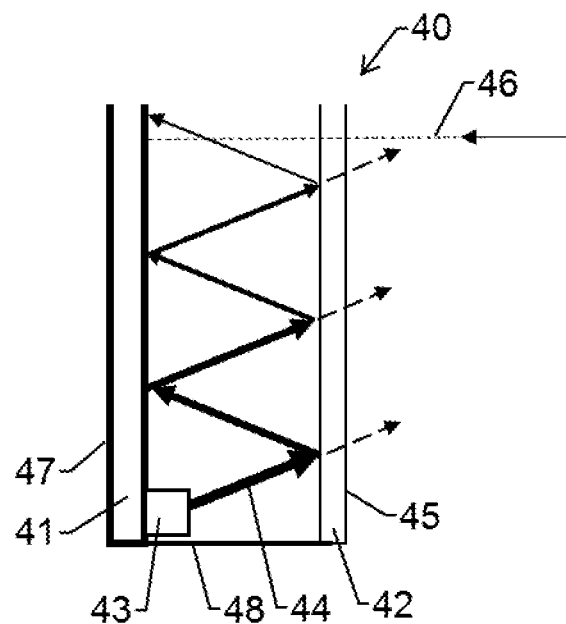
FIG. 6 shows an embodiment of an infinity mirror.

Further, the capture device 10 comprises an infinity mirror 40. The infinity mirror 40 is shown in FIG. 6 in more detail. The infinity mirror 40 comprises at least two mirror surfaces 41,42 which are arranged opposite apart from each other. A light source 43 is arranged for emitting light 44. The mirror 40 also comprises a front side 45 to look inside the infinity mirror 40. Here, the two mirror surfaces 41,42 are built as separate mirrors 41,42.

In one alternative embodiment, the infinity mirror can be provided by a single optical element which comprises the two mirror surfaces 41,42. For example, the two mirror surfaces 41,42 are provided by coated boundary surfaces of a glass element having defined width.

The infinity mirror 40 is arranged at the capture device 10 and placed and oriented relative to the capture device 10 so that an insight axis 46 and an insight distance for the person is defined to provide suitable and repeatable measuring of the skin of the person by defined looking inside the infinity mirror 40.

At least one of the mirror surfaces is built as semi-transparent mirror 42 and is arranged on the front side 45. The infinity mirror 40 comprises the front side and an opposite infinity side 47. The front side 45 and an infinity side 47 are connected by side walls 48. The front side 45 is arranged opposite apart of the infinity side 47.

The light source 43 provides emitting of illumination light inside the infinity mirror 10.

The semi-transparent mirror 42 can be built to be 50% reflective and 50% transmissive, i.e. a portion of 50% of the light emitted by the light source 43 is transmitted to the outside of the infinity mirror 40 and a remaining portion of 50% of the emitted light is reflected back to the other mirror 41.

The backside mirror surface 41 is built as an (totally) reflective mirror 41 and is arranged on the infinity side 47.

The light emitted by the light source 43 bounces forth and back between the mirrors 41, 42. Each time the light impinges on the semi-transparent mirror 42 some portion of the light escapes the front mirror 42. Each time a part of the light escapes through the front mirror 42, less amount of light is reflected towards the back mirror 41. Due to this effect, an user of the device 10 sees progressively dimmer "illusion" light sources behind the real light source 43 when looking into the infinity mirror on side of the front mirror 42.

In the present embodiment a number of LEDs is arranged around the perimeter of the infinity mirror 40 to provide circumferential illumination inside of the infinity mirror 40. The mirrors 41 and 42 are preferably arranged with a relative distance to each other out of a range of 20 mm to 30 mm. The configuration of the infinity mirror 40 provides an optical effect if looking into an illuminated tunnel which comprises an infinite end of the tunnel in the centre; in other words: the tunnel tapering in infinity. Such an appearance inside of the infinity mirror 40 occurs in case the user of the device 10 is in desired position and orientation relative to the infinity mirror 40 and looks inside the mirror 40 according to a corresponding viewing direction (insight axis 46).

Such design provides a defined alignment of a person in front of the device 10. A measurement of the person by means of the illumination elements and cameras can be performed when the person sees the tunnel inside of the infinity mirror 40 entirely, i.e. the person sees the side walls and the infinite end of the tunnel basically in the centre of the infinity mirror 40. This additionally provides repositioning of the person in front of the device 10 in identical position and orientation. This provides a big advantage when a later progress measurement of the person's face should be performed, e.g. after a particular treatment of the person's face. Hence, comparison of before/after states of the face becomes comparatively direct and with low effort.

Furthermore, the infinity mirror 40 provides that the person to be measured can be guided relative to the capture device 10 in short distance. Also, squinting of the person is avoided due to the optical effect of the infinity mirror 40, i.e. looking into infinity. In other words, compared to other approaches of positioning a person with short distance relative to a device to capture an image of the face of the person, the use of an infinity mirror provides removal of squinting of the person for capturing the image. This results in providing image data which represents the person in more realistic manner, i.e. true-to-life.

The insight axis 46 is defined by the surface the front mirror 42, wherein the insight axis 46 is perpendicular to and intersects a centre point of the surface of the front mirror 42.

The insight distance, i.e. a desired distance between the person to be measured and the capture device 10, is defined by the configuration of the infinity mirror, in particular by the relative arrangement of the at least two mirrors and the LEDs.

A visual output at the capture device 10 can be provided to show the person a measure concerning an alignment deviation relative to the capture position. As for example, the output may comprise coloured markings the colour of which switches in case the person approaches or reaches the capture position in one or each direction relative to the device 10.

Figure 7:
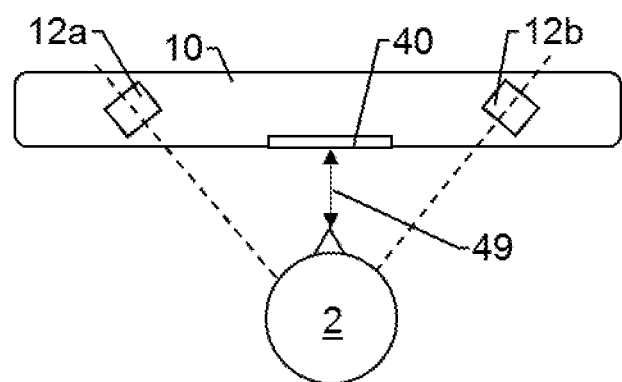
FIG. 7 shows an embodiment of a capturing device.

FIG. 7 shows a crosscut of the capture device 10 with the infinity mirror 40 and a person 2 (object) to be captured in a top view direction. As can be seen, by the particular arrangement of the optical axes of the cameras 12*a* and 12*b*, the face of the person 2 can be captured from two direction in a way so that the face can entirely be covered by the generated image data. In particular, the entire region of interest e.g. for facial cosmetic treatment can be covered, e.g. the front side, left and right face half and neck.

Furthermore, the infinity mirror 40 provides positioning of the person 2 according to the insight distance 49. The insight distance 49 is given by the (interior) design of the infinity mirror, e.g. by a distance between the front 42 and the backside mirror 41 and an arrangement of the light source 43 relative thereto.

In the shown embodiment, the infinity mirror 40 is designed so that the insight distance 49 is comparatively short to provide close positioning of the person 2 relative to the device 10. Such close positioning becomes suitable because the infinity mirror 40 provides looking of the person into infinity and thus squinting can be avoided despite the short insight distance 49.

Although aspects are illustrated above, partly with reference to some preferred embodiments, it must be understood that numerous modifications and combinations of different features of the embodiments can be made. All of these modifications lie within the scope of the appended claims.

The invention claimed is:

1. A capture device for imaging a person, the capture device comprises at least one camera for capturing an image of the person, the capture device comprises an infinity mirror comprising:
   at least two mirror surfaces arranged oppositely from each other,
   a light source for emitting light, and
   a front side to look inside the infinity mirror, and
   the infinity mirror is arranged at the capture device and placed and oriented relative to the capture device so that
      a capture range with an insight axis and an insight distance for the person is defined and
      defined capturing of the person by means of the at least one camera is provided when the person is positioned according to the capture range.

2. The capture device according to claim 1, wherein a defined inner appearance of the inside of the infinity mirror is associated with the capture range and the infinity mirror is arranged at the capture device and placed and oriented relative to the capture device so that:
   guiding of the person is provided by looking inside the infinity mirror and simultaneously adjusting the relative position of the person until the defined inner appearance is observed by the person, and
   accurately positioning of the person is provided when the person is positioned according to the capture range.

3. The capture device according to claim 1, wherein the insight axis is defined by a surface of at least one of the two mirror surfaces, in particular the insight axis is perpendicular to and intersects a centre point of the surface of the at least one of the two mirror surfaces.

4. The capture device according to claim 1, wherein the insight distance is defined by the configuration of the infinity mirror, in particular the relative arrangement of the at least two mirror surfaces and the light source.

5. The capture device according to claim 1, wherein the infinity mirror provides an inner appearance which appears to be a tunnel tapering in infinity and provides required aligning for the person relative to the capture device when the inner appearance is entirely observable by the person, in particular when all sides of the tunnel are observable.

6. The capture device according to claim 1, wherein the infinity mirror, in particular the inner appearance, provides avoiding of squinting of the person in the course of capturing the person.

7. The capture device according to claim 1, wherein the infinity mirror, in particular the inner appearance, provides to capture the person with low distance between the person and the capture device and without squinting of the person.

8. The capture device according to claim 1, wherein at least one of the mirror surfaces is built semi-transparent and is arranged on the front side.

9. The capture device according to claim 1, wherein the infinity mirror comprises the front side and an infinity side, wherein the front side is arranged opposite apart of the infinity side and at least one of the mirror surfaces is built reflective and is arrange on the infinity side, in particular wherein the front side and an infinity side are connected by side walls.

10. The capture device according to claim 1, wherein the light source is arranged between or in front of the mirror surfaces, in particular in front of the front side.

11. The capture device according to claim 1, wherein the light source is arranged closer to the front side than to the infinity side.

12. The capture device according to claim 1, wherein the light source is provided by a number of LEDs which are circumferentially arranged around the centre of the infinity mirror, in particular along the perimeter of the infinity mirror.

13. A measuring system for measuring the skin of a person, the measuring system comprising:
   a capture device according to claim 1, and
   a controlling and processing unit comprising at least:

a data acquisition functionality which is configured to provide surface data by capturing at least one image by detecting the skin by means of at least one camera, and a 3D-modelling functionality which is configured to provide a 3D model of the skin by processing the surface data.

14. The measuring system according to claim 13, further comprising a display device having a display and being configured to display the 3D model on the display.

15. The measuring system according to claim 13, wherein the capture device comprises at least one illumination element for illuminating the skin with measuring light.

16. The measuring system according to claim 13, wherein the controlling and processing unit comprises a guiding functionality which is configured to
   provide a guiding output, in particular an acoustic guiding output and/or a visual guiding output, to guide the person to approach the defined capture range relative to the capture device, and
   control or notice the execution of the data acquisition functionality as a function of a deviation of a position of the person from the capture range.

17. The measuring system according to claim 16, wherein the guiding output is derived based on image-based or video-based monitoring of the person by means of the at least one camera and image processing the camera data generated in the course of the monitoring.

18. A guiding device for accurately positioning a person, in particular the face or a part of the face of the person, relative to the guiding device, the guiding device comprising:
   a camera for capturing an image of the person, and
   a controlling and processing unit,
   an infinity mirror with:
      at least two reflective surfaces arranged oppositely from each other
      a light source for emitting light, and
      a front side to look inside the infinity mirror,
   wherein the infinity mirror is arranged at the guiding device and placed and oriented relative to the guiding device so that:
      a capture range with an insight axis and an insight distance range for the person is defined, wherein a defined appearance of the inside of the infinity mirror is associated with the capture range,
      guiding of the person is provided by looking inside the infinity mirror and simultaneously adjusting the relative position of the person until the defined appearance is observed by the person, and
      accurately positioning of the person is provided when the person is positioned according to the capture range, and
   the controlling and processing unit comprises a guiding functionality which is configured to:
      derive a guiding output based on image-based or video-based monitoring of the person by means of the camera and process the camera data generated in the course of the monitoring, and
      provide the guiding output, in particular an acoustic guiding output and/or a visual guiding output, to guide the person to approach the defined capture range relative to the guiding device.

* * * * *